United States Patent
Vescovi et al.

(10) Patent No.: US 10,106,779 B2
(45) Date of Patent: Oct. 23, 2018

(54) METHOD FOR THE ISOLATION FOR MAMMALIAN STEM CELLS AND USES THEREOF

(71) Applicant: Hyperstem SA, Lugano (CH)

(72) Inventors: Angelo Luigi Vescovi, Maroggia (CH); Elena Binda, Bergamo (IT)

(73) Assignee: HYPERSTEM SA, Lugano (CH)

( * ) Notice: Subject to any disclaimer, the term of this patent is extended or adjusted under 35 U.S.C. 154(b) by 0 days.

(21) Appl. No.: 14/443,834

(22) PCT Filed: Nov. 19, 2013

(86) PCT No.: PCT/EP2013/074166
§ 371 (c)(1),
(2) Date: May 19, 2015

(87) PCT Pub. No.: WO2014/076302
PCT Pub. Date: May 22, 2014

(65) Prior Publication Data
US 2015/0299664 A1    Oct. 22, 2015

(51) Int. Cl.
C12N 5/16       (2006.01)
G01N 33/483     (2006.01)
C12N 5/095      (2010.01)
G01N 33/50      (2006.01)

(52) U.S. Cl.
CPC ....... *C12N 5/0695* (2013.01); *G01N 33/5011* (2013.01); *G01N 33/5073* (2013.01); *G01N 2333/715* (2013.01)

(58) Field of Classification Search
None
See application file for complete search history.

(56) References Cited

FOREIGN PATENT DOCUMENTS

WO    2012042021    4/2012
WO    WO 2012/042021  *  4/2012

OTHER PUBLICATIONS

Genander and Frisén, Current Opinion in Cell Biology, 22:611-616, 2010.*
Binda et al., Cancer Cell, 22(6):765-780, Dec. 10, 2012.*
Amendola et al., Coordinate dual-gene transgenesis by lentiviral vectors carrying synthetic bidirectional promoters, Nature Biotechnology, vol. 23, No. 1, Jan. 2005, pp. 108-116.
Binda et al., The EphA2 Receptor Drives Self-Renewal and Tumorigenicity in Stem-like Tumor-Propagating Cells from Human Glioblastomas, Cancer Cell, vol. 22, Issue 6, Dec. 11, 2012, pp. 765-780.
Galli et al., Isolation and Characterization of Tumorigenic, Stem-like Neural Precursors from Human Glioblastoma, Cancer Research, vol. 64, Oct. 1, 2004, pp. 7011-7021.
Goichberg et al., The Ephrin A1-EphA2 System Promotes Cardiac Stem Cell Migration After Infarction, Circulation Research, vol. 108, Apr. 29, 2011, pp. 1071-1083.
Hu et al., ELDA: Extreme limiting dilution analysis for comparing depleted and enriched populations in stem cell and other assays, Journal of Immunological Methods, vol. 347, 2009, pp. 70-78.
Jenkins et al., Bioluminescent human breast cancer cell lines that permit rapid and sensitive in vivo detection of mammary tumors and multiple metastases in immune deficient mice, Breast Cancer Research, vol. 7, No. 4, 2005, pp. 444-454.
Lazarova et al., Growth Factor Receptors in Hematopoietic Stem Cells: EPH Family Expression in CD34+ and CD133+ Cell Populations from Mobilized Peripheral Blood, Internatl. Journal of Immunopathology and Pharmacology, vol. 19, No. 1, 2006, pp. 49-56.
Vescovi et al., Isolation and Cloning of Multipotential Stem Cells from the Embryonic Human CNS and Establishment of Transplantable Human Neural Stem Cell Lines by Epigenetic Stimulation. Experimental Neurology, vol. 156, 1999, pp. 71-83.
European search report and European search opinion for European application No. 12193206, dated Mar. 27, 2013, 9 pages.

* cited by examiner

*Primary Examiner* — Kimberly Ballard
*Assistant Examiner* — Stacey N MacFarlane
(74) *Attorney, Agent, or Firm* — McCarter & English, LLP; Beverly W. Lubit

(57) ABSTRACT

The present invention concerns the field of stem cell biology, and in particular relates to a method for producing an isolated bona fide population of mammalian stem cells, and uses of the stem cells thus produced. Human glioblastomas (hGBMs) have now been shown to contain a minor subset of cells bearing the defining features of somatic stem cells (SCs) and the ability to establish, expand and perpetuate these tumors. They are defined stem-like tumor propagating cells (TPCs). This has caused a paradigmatic shift in the way we interpret hGBM physiology, for it identifies TPCs as a major culprit to be tackled for the development of novel therapeutics. It also suggests that studying the regulatory mechanisms of normal neurogenesis may point to specific inhibitors of TPCs.

15 Claims, 15 Drawing Sheets

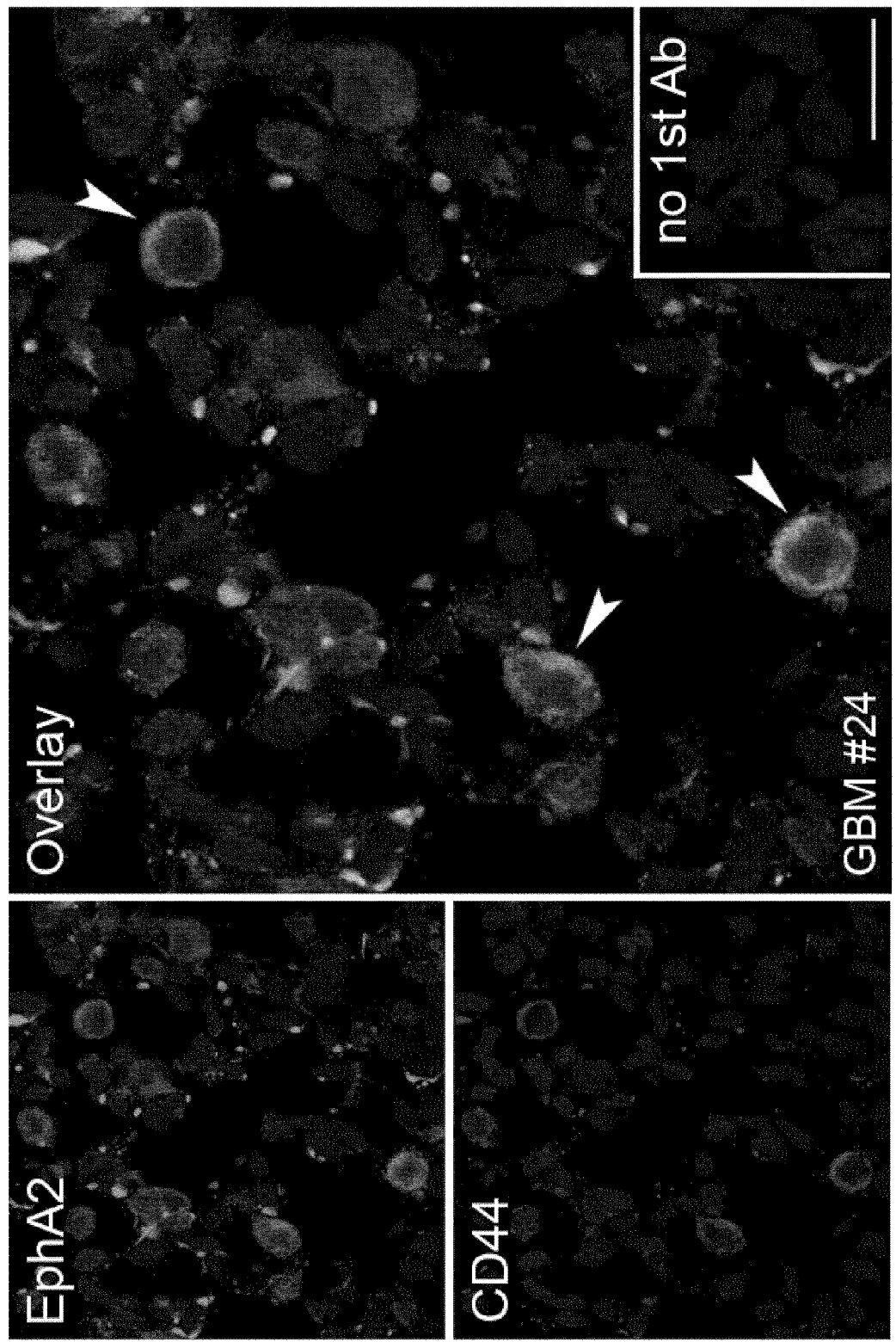

FIGURE 2G

| Tissue | Population | Number of tumors/Number of injections | | | GBM-Initiating cell frequency (95% confidence interval) | | Median Survival (days) |
|---|---|---|---|---|---|---|---|
| | | Cells per injection | | | | | |
| | | 40,000 | 20,000 | 10,000 | | | |
| GBM #23 | EphA2$^{High}$ | 9/9 | 9/9 | 9/9 | 1/1 | > 1/6961 | 128 |
| | EphA2$^{Low}$ | 9/9 | 5/9 | 3/9 | 1/18500 | (1/30932-1/11065) | ∞ |
| GBM #25 | EphA2$^{High}$ | 8/8 | 8/8 | 8/8 | 1/1 | > 1/7411 | 136 |
| | EphA2$^{Low}$ | 8/8 | 3/8 | 2/8 | 1/24060 | (1/42246-1/13703) | ∞ |
| All | | 17/17 | 17/17 | 17/17 | 1/1 | > 1/5152 | 132±5 |
| | | 17/17 | 8/17 | 5/17 | 1/20943 | (1/30580-1/14344) | ∞ |
| GBM #22 | EphA2$^{High}$ / SSEA-1$^{High}$ | 9/9 | 9/9 | 9/9 | 1/1 | > 1/6961 | 164 |
| | EphA2$^{Low}$ / SSEA-1$^{Low}$ | 9/9 | 4/9 | 3/9 | 1/20820 | (1/35015-1/12380) | ∞ |
| GBM #24 | EphA2$^{High}$ / CD44$^{High}$ | 11/11 | 11/11 | 11/11 | 1/1 | > 1/6290 | 187 |
| | EphA2$^{Low}$ / CD44$^{Low}$ | 11/11 | 5/11 | 3/11 | 1/21696 | (1/34806-1/13524) | ∞ |
| All | | 20/20 | 20/20 | 20/20 | 1/1 | > 1/4813 | 176±12 |
| | | 20/20 | 9/20 | 6/20 | 1/21296 | (1/30211-1/15011) | ∞ |

METHOD FOR THE ISOLATION FOR MAMMALIAN STEM CELLS AND USES THEREOF

FIELD OF THE INVENTION

The present invention concerns the field of stem cell biology, and in particular relates to a method for producing an isolated population of bona fide mammalian stem cells, and uses of the stem cells thus produced.

STATE OF THE ART

Stem cells are the primary cells of each pluricellular organism. The two main categories of human stem cells are embryonic (ESC), derived from the inner cell mass of the blastocyst, and somatic stem cells (SC) derived from fetal or adult tissues. The former are able to originate all the cell phenotypes of the organism since they are deputated to the development of all the tissues, while the adult somatic SC originate the cell lineages of the tissue of origin and contribute to tissue homeostasis and repair. The definition of a cell as stem mainly requires the fulfillment of two properties: the capacity to extensively proliferate while maintaining an undifferentiated and stable phenotype, defined as "self-renewal", and to differentiate in multiple cell lineages "multipotentiality". The last is variably defined according to the source of SC.

In summary, stem cells, by the simplest definition, are a unique distinguishable population of cells that possess the ability to self-renew, proliferate and differentiate into specialized tissues.

Hematopoietic stem cells (HSC) are the most studied of the adult stem cells and have enjoyed the most successful translation to the clinic. HSCs can be divided into two classes of cells, namely long-term and short-term repopulating cells, with the progeny of these cells being able to differentiate into the repertoire of blood cell lineages.

In addition to the HSC, adult stem cells have also been extensively studied in the skin, small intestines and more recently they have been identified in the muscle, liver, prostate, breast, heart and brain. In general, all these tissue compartments share the presence of a low frequency cell that has the ability to proliferate and to generate new cells going to replace those lost to injury, disease and normal cell turnover, thus contributing to the lifespan tissue homeostasis.

Although historically the one tissue where stem cells should not be found was the brain, adult neurogenesis has now been demonstrated in the adult human brain, persisting in discrete central nervous system (CNS) regions.

Neural stem cells (NSCs) are the most primitive neural cells in the CNS. Because most mature neural cells, with particular reference to neurons, are very specialized cells and they are quite sensitive to environmental changes, such as oxygen conditions or ex-citotoxic molecules, the importance of NSC in sustaining the development and homeostasis of the nervous tissue is essential. The slow turnover of degenerating with newly generated neuronal cells under physiological condition in vivo has highlighted that NSC basically rest in a state of quiescence, which allows to maintain a steady balance between the ability to undergo self-renewal and to differentiate without depleting the stem pool.

One of the most prominent topics in the field of cancer biology and therapy is that a small percentage of cells with the cardinal properties of stem cells, called cancer stem cells (CSCs) or tumor-propagating cells (TPCs), are responsible for the origin and maintenance of solid malignancies.

Malignant gliomas are the most commonly diagnosed adult primary tumors of the CNS and their incidence is increasing world-wide. In general, they are not curable tumors, with most patients succumbing to their disease regardless of treatment. Grade IV glioma, glioblastoma multiforme (GBM), is the most malignant and common glioma with a median survival time of 9-15 months despite aggressive therapy that combines state-of-art imaging with surgery, radiotherapy and chemotherapy.

The study of somatic stem cells certainly would help toward an understanding of the cellular elements responsible for cancer progression and resistance to treatment, and the advantage of studying single or defined population of cells, as opposed to large or less defined populations, will likely benefit not only the understanding of the contribution that different population make towards tumor growth and resistance but will also allow a more detailed and accurate mapping of tumor heterogeneity.

Many attempts have been made for an efficient isolation of bona fide stem cells, which need to be in a sufficient number and in the necessary conditions for expansion.

Brain tumor-propagating cells share characteristics similar to those of normal NSCs, including the expression of several markers, the ability for self-renewal and differentiation, and signaling pathways involved in the regulation of cellular survival and proliferation. Hence, the study of regulatory mechanisms of normal neurogenesis may lead to the identification of novel inhibitors of brain TPCs and may result in the development of novel and more specific therapeutic strategies for brain cancer.

To date, no cell marker is absolute in identifying normal NSCs, nor in identifying brain TPCs.

Not all tumor cells, that are marker positive, are brain TPCs and not all brain TPCs express known markers. For instance, for several types of brain tumor, including a subgroup of primary GBM, TPCs were found to express CD133. However, CD133 does not appear to be essential for stem cell-like properties, as subgroups of GBM driven by CD133-TPCs have recently been identified.

The need and importance is increasingly felt for identifying a method, which allows to isolate and obtain a population of bona fide stem cells, which maintain an undifferentiated and stable phenotype (self-renewal), retain the capability to differentiate in multiple cell lineages and may be used in applications as different as regenerative medicine and drug discovery.

Thus it is therefore object of the present invention to provide a method, which allows the efficient isolation of bona fide SCs or TPCs mammalian stem cells.

SUMMARY OF THE INVENTION

The present invention concerns a method for producing an isolated population of bona fide mammalian stem cells comprising the steps of:
  a. providing a population of cells,
  b. selecting from the population of cells of step a. the cells that express EphA2;
  c. isolating the cells selected in step b.,
  thereby producing a population of bona fide SCs or TPCs mammalian stem cells.

As will be further described in the detailed description of the invention, the method of the present invention has the advantages of allowing the isolation of an isolated population of bona fide mammalian stem cells.

The present relates to the isolated population of bona fide mammalian stem cells obtainable by the method of the invention.

A further aspect of the present invention is the use of the isolated population of bona fide mammalian stem cells according to the invention, for the screening of a compound having an inhibiting activity on growth of said stem cells.

A still further aspect of the present invention is the use of EphA2 as a cell surface marker for the identification and the isolation of a stem cell.

BRIEF DESCRIPTION OF THE DRAWINGS

The characteristics and advantages of the present invention will be apparent from the detailed description reported below, from the Examples given for illustrative and non-limiting purposes, and from the annexed FIGS. 1-2, wherein.

Figure 1A:
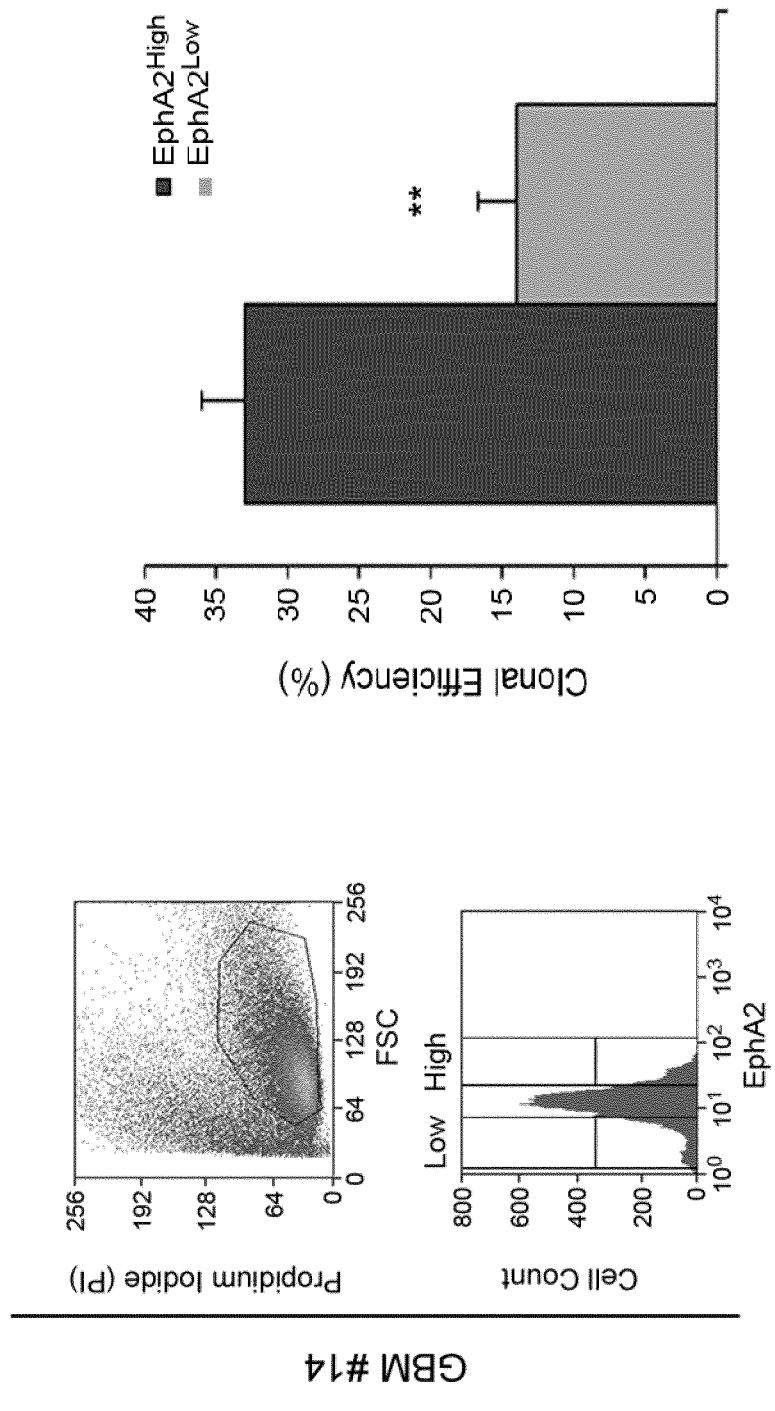
FIG. 1: Shows Enrichment of the Stem-like Tumorigenic Pool Based on EphA2 Levels (A) Viable (propidium iodide negative) tumor cells acutely isolated from hGBM specimens or established human normal neural stem cells (top left) were sorted into $EphA2^{High}$ and $EphA2^{Low}$ fractions (bottom left). The $EphA2^{High}$ fraction displayed higher clonogenic index than the $EphA2^{Low}$ fraction (right) (n=4 tumors). Error bars: SEM; **p=0.0004 for $EphA2^{High}$ vs. $EphA2^{Low}$ by Student's t test.
Figure 1B:
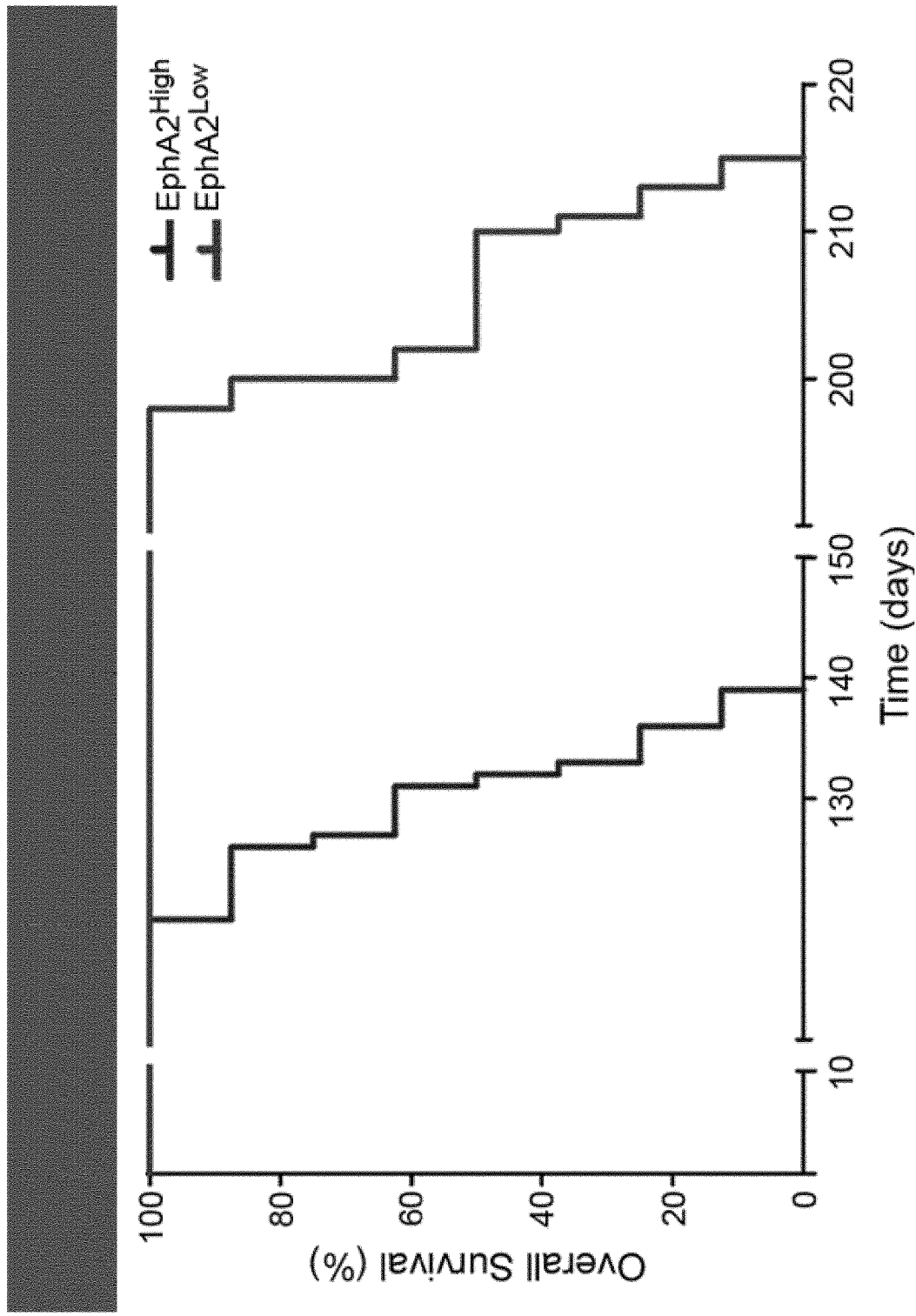
Figure 1C:
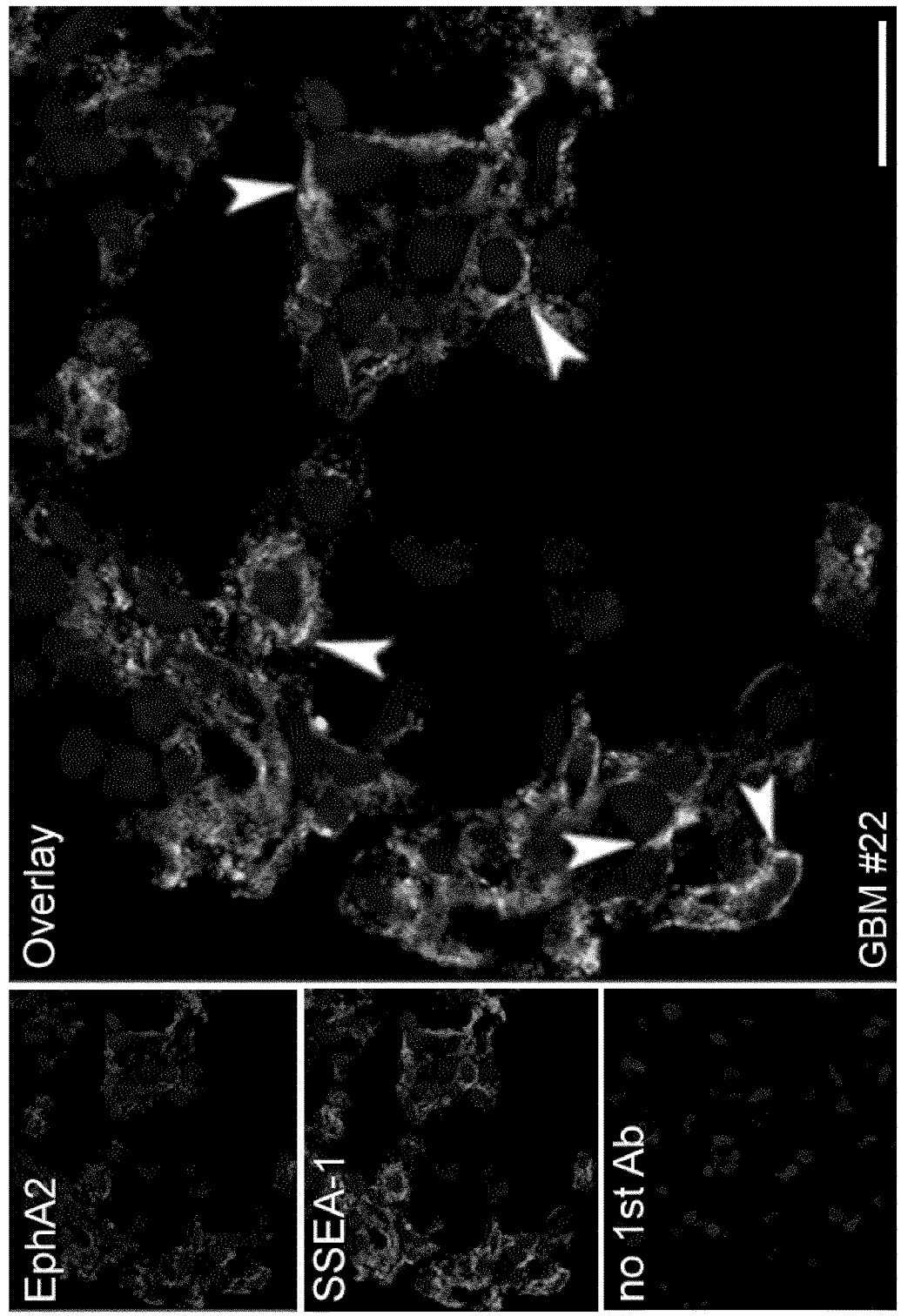
Figure 1D:
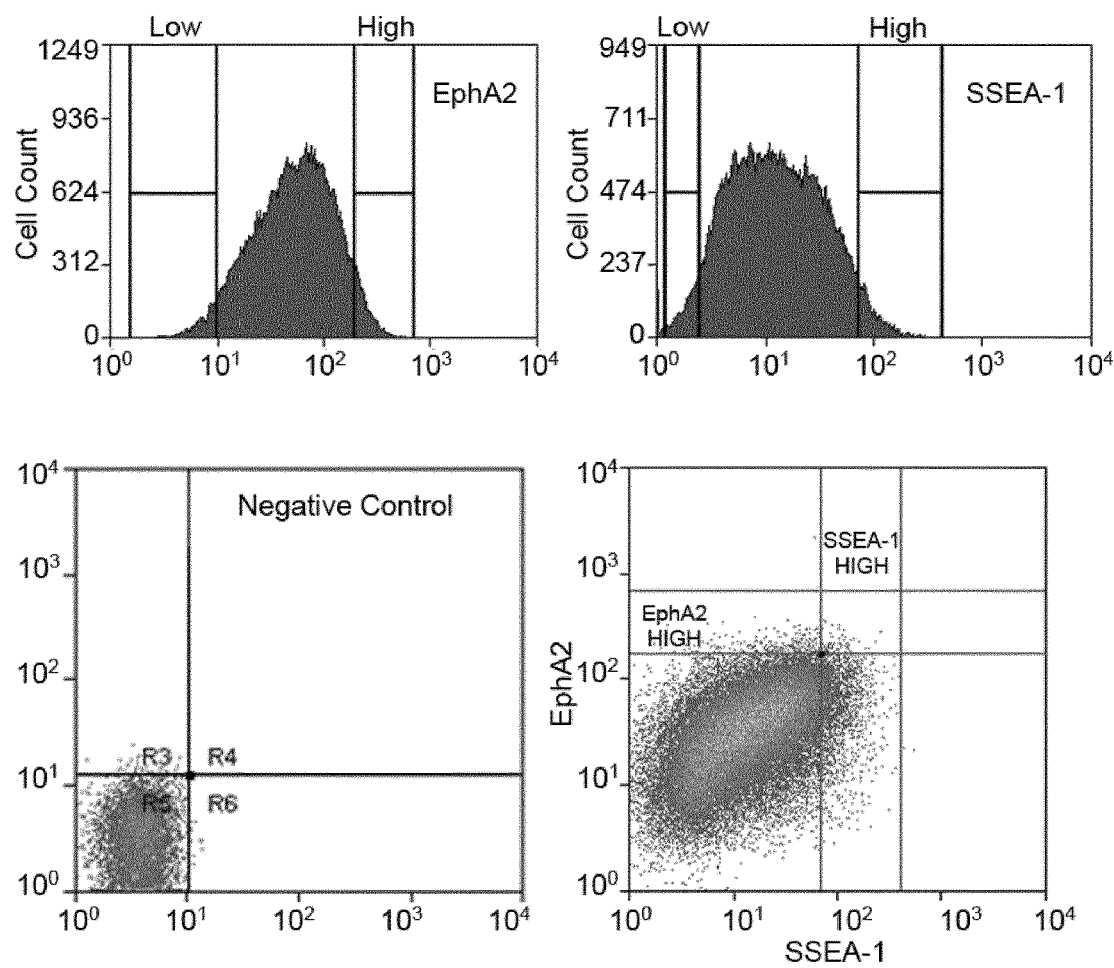
Figure 1E:
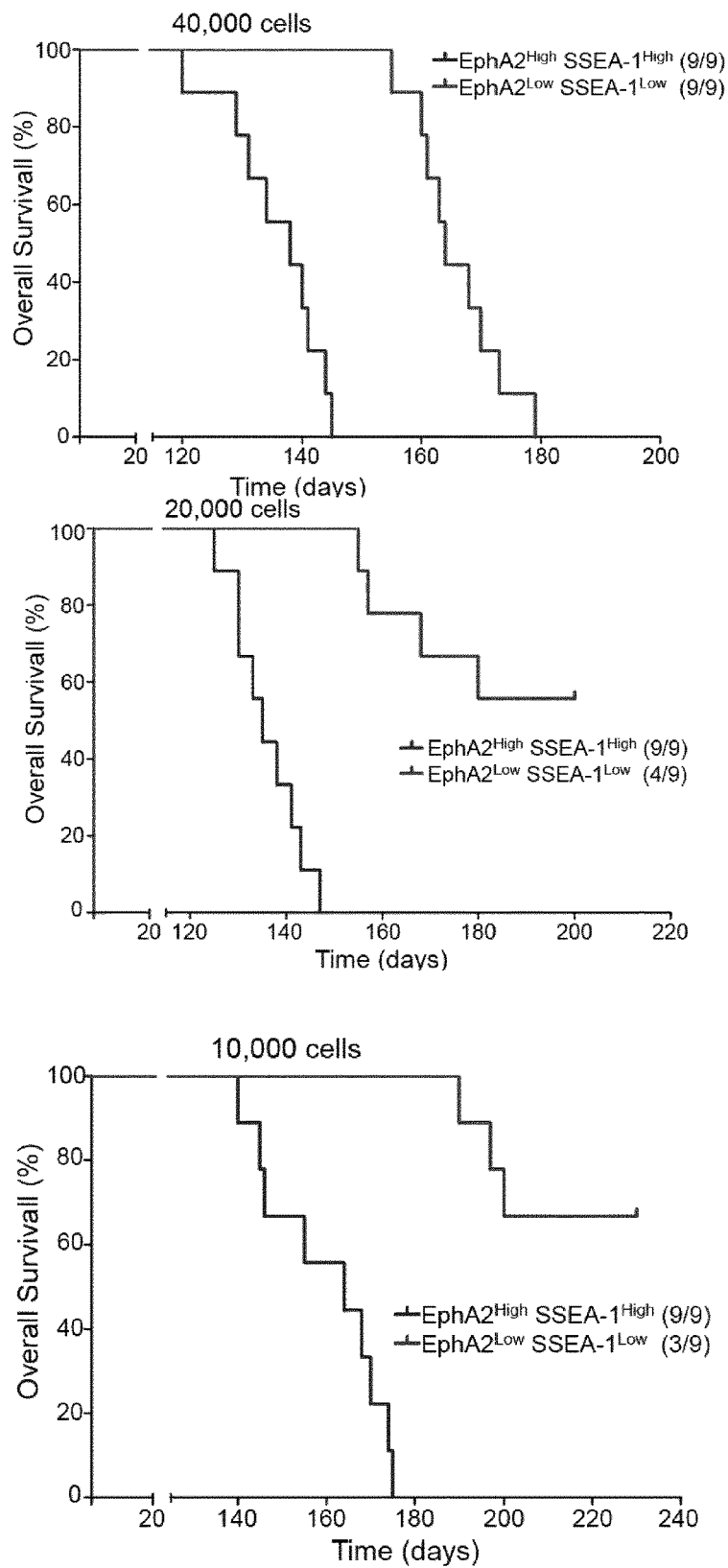
Figure 1F:
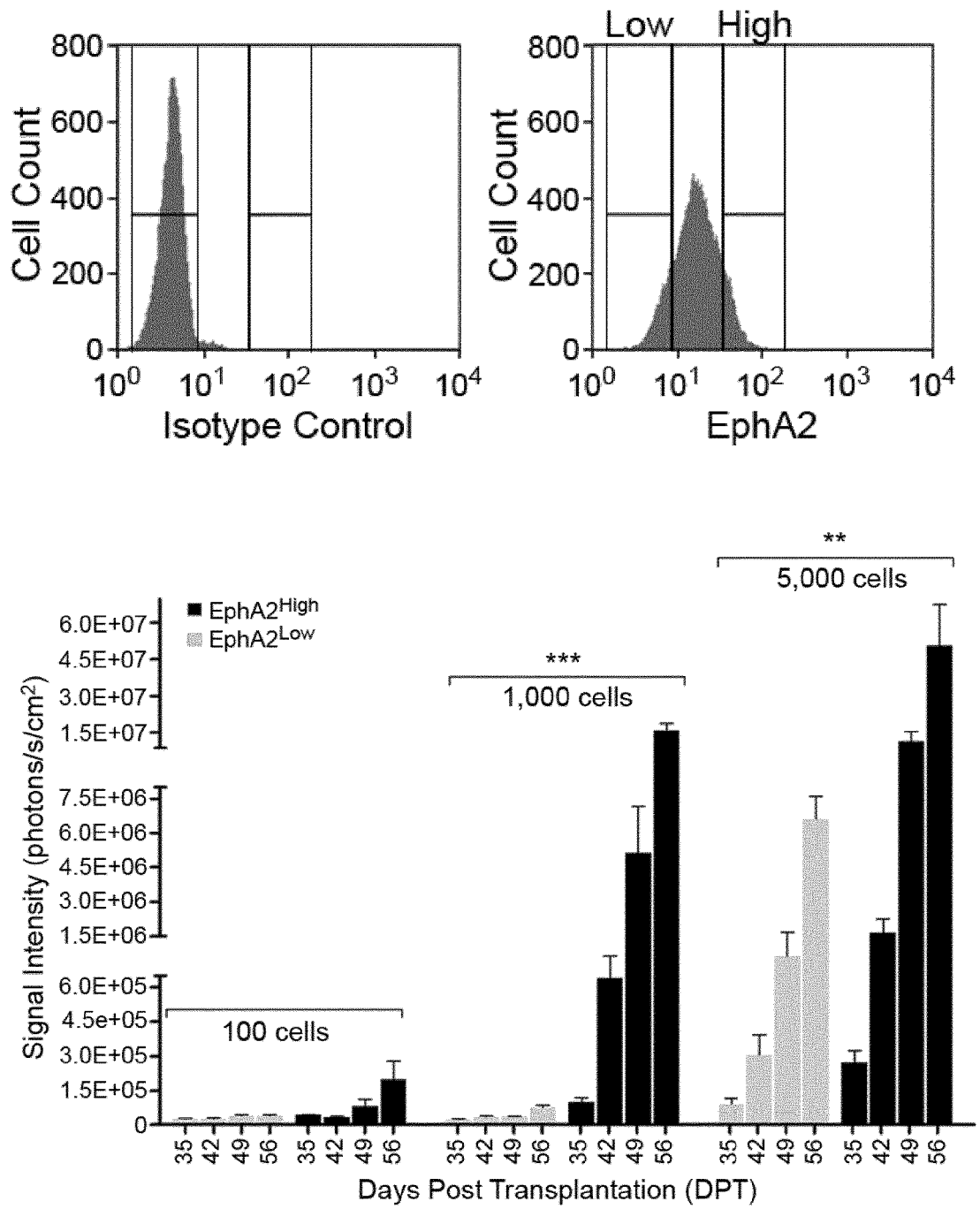
Figure 1G:
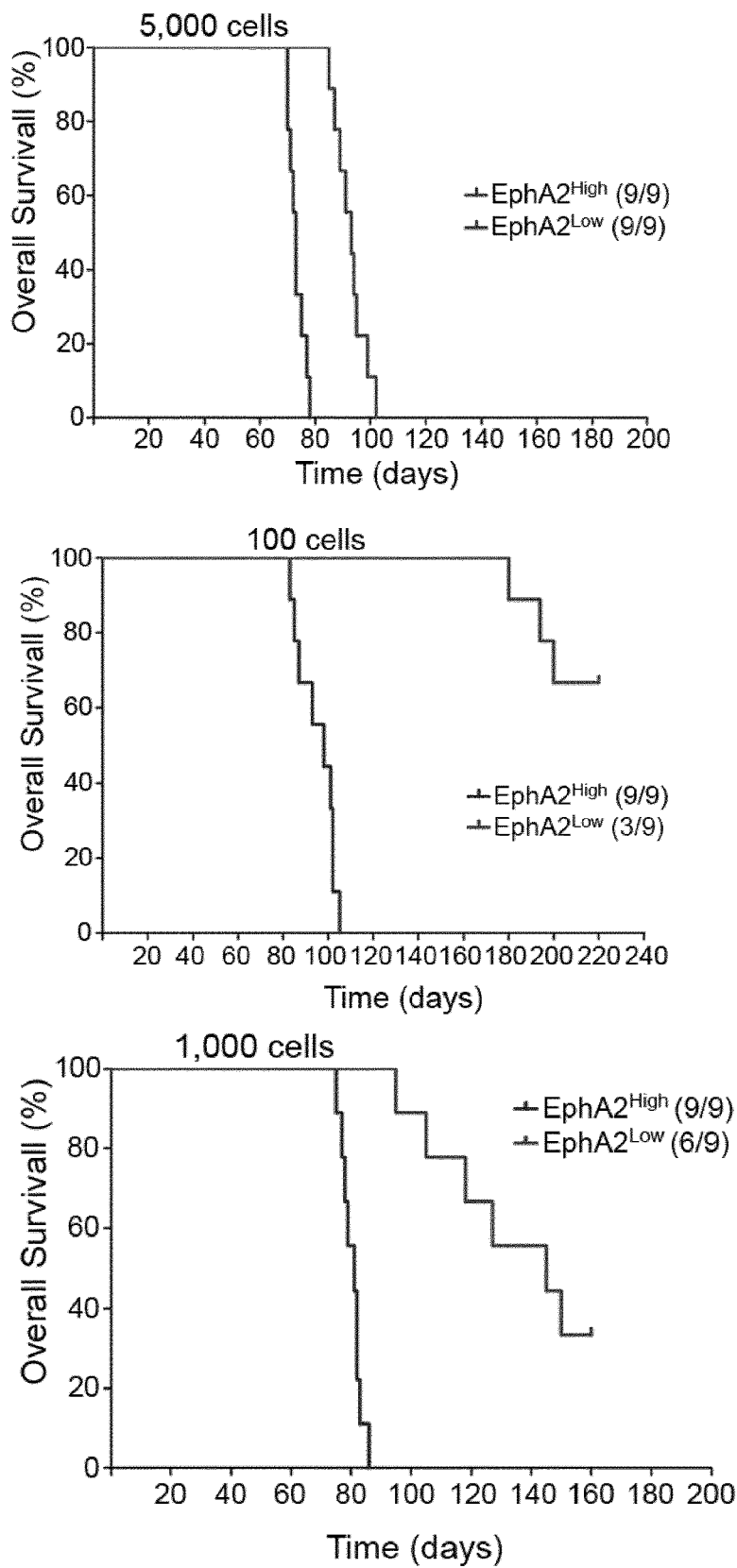
Figure 2A:
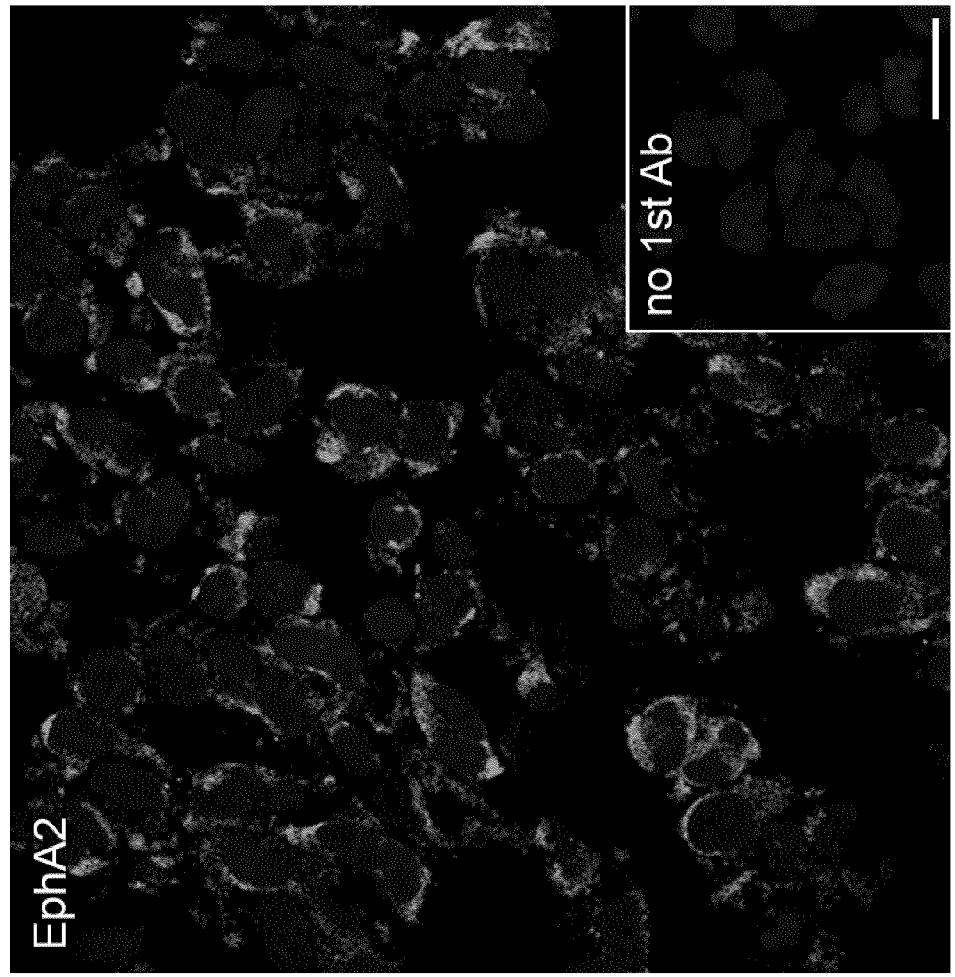
Figure 2B:
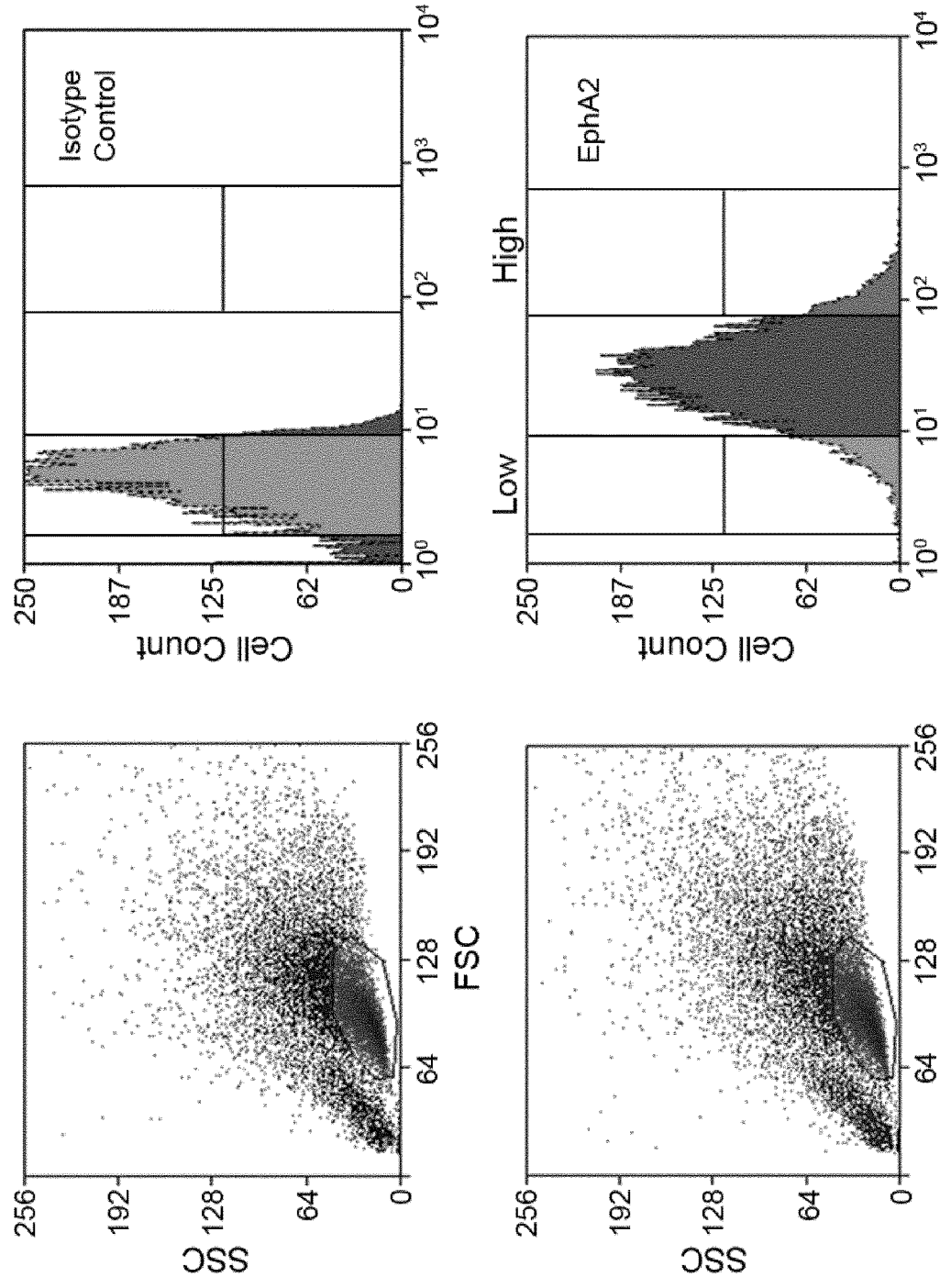
Figure 2C:
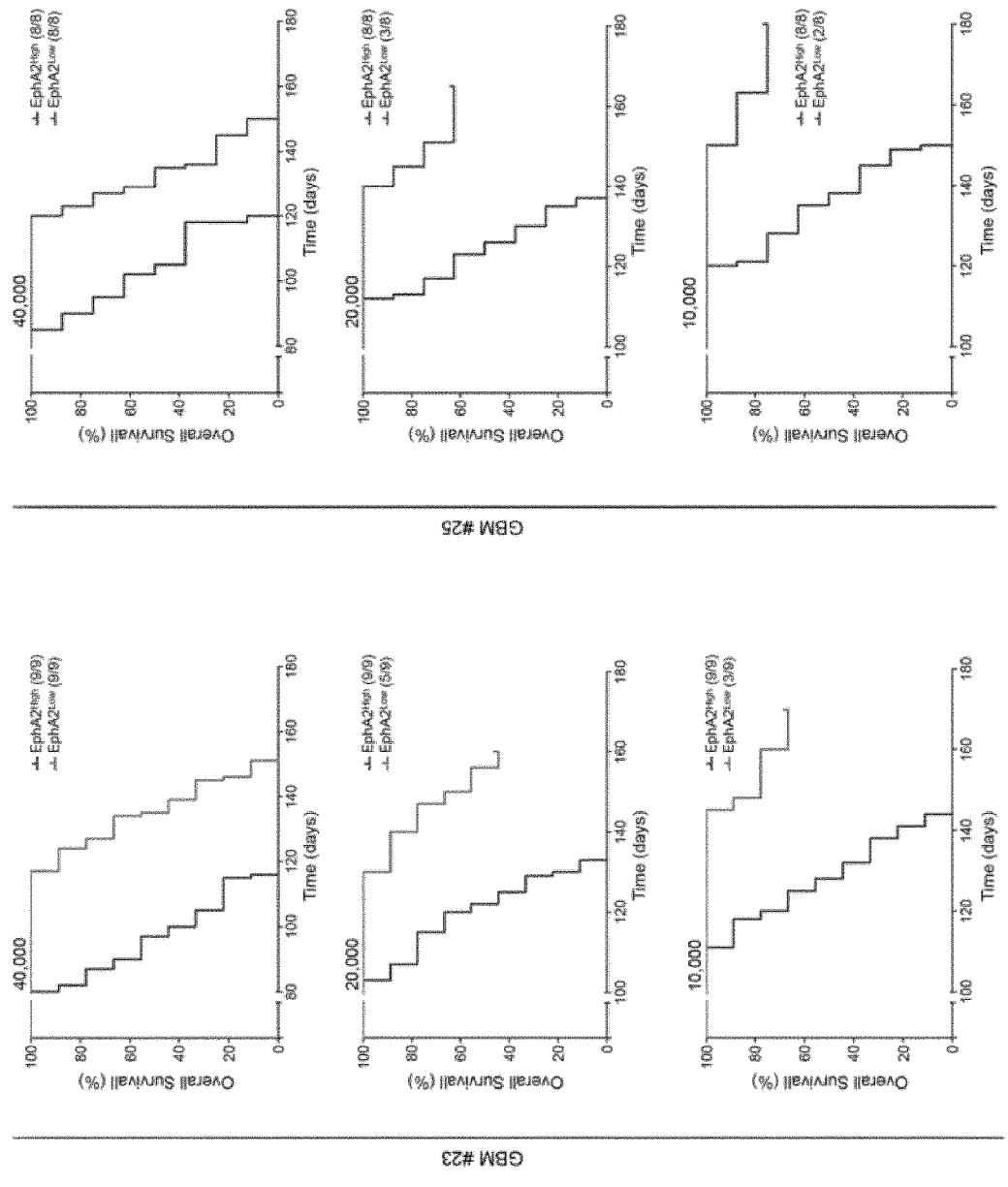
Figure 2E:
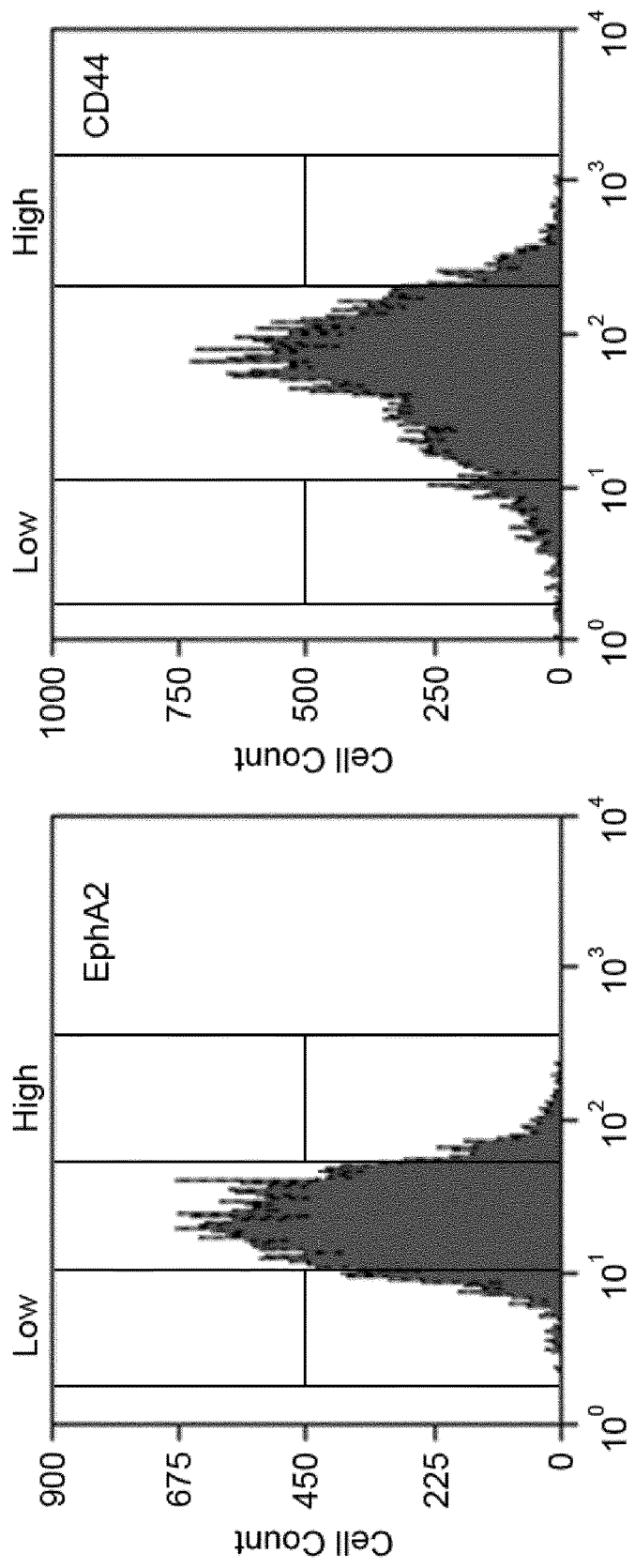
Figure 2F:
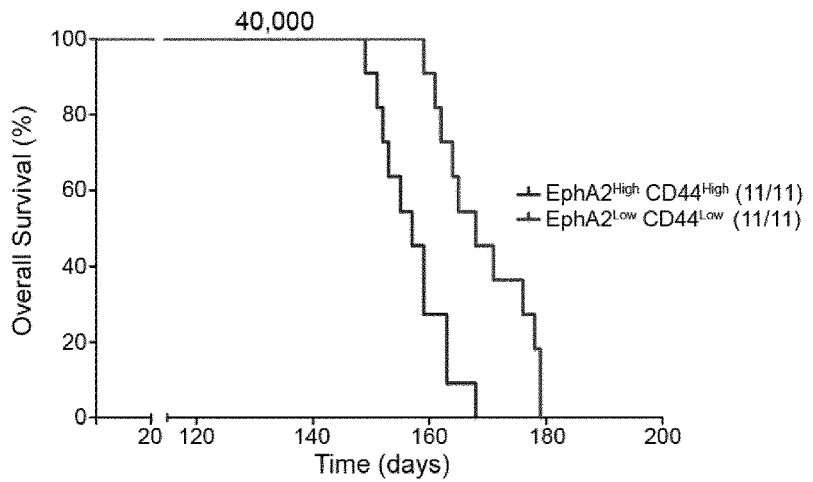
Figure 2F:
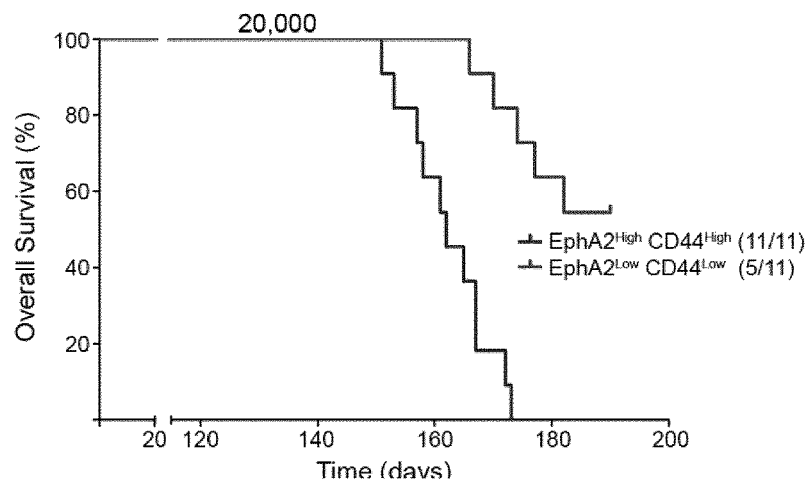
Figure 2F:
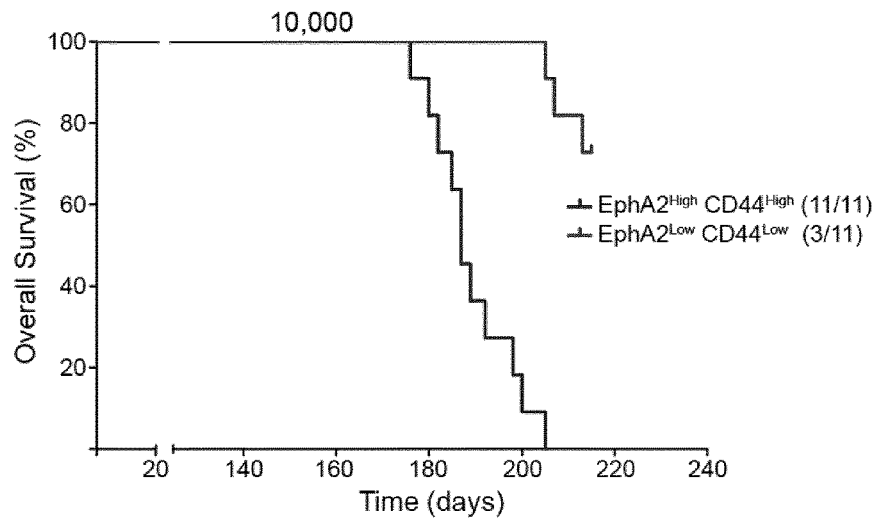

(B) Intracranial transplantation of $6 \times 10^4$ $EphA2^{High}$ or $EphA2^{Low}$ cells confirmed the much higher tumor-propagating capacity of the former (MC test, log-rank p-value <0.0001 for $EphA2^{High}$ vs. $EphA2^{Low}$; n=8).

(C) Confocal images show widespread co-localization (arrowheads; yellow) of EphA2 (red) and SSEA-1 (green) in hGBM tissue. Bar, 20 µm.

(D) Cells from the same hGBM were sorted and gated according to EphA2 and SSEA-1 levels.

(E) Kaplan-Meier survival curves show that mice receiving intracranially $2 \times 10^4$ and $1 \times 10^4$ $EphA2^{High}$ SSEA-$1^{High}$ purified TPCs die earlier (median survival: 135 and 164 days, respectively) than mice receiving $EphA2^{low}$ SSEA-1Low cells (56% and 67% survival at 230 days, respectively). MC and GBW tests, log rank p-value <0.0001 $EphA2^{High}$ SSEA-$1^{High}$ vs. $EphA2^{low}$ SSEA-$1^{low}$; n=9). Survival was also shorter when implanting $4 \times 10^4$ $EphA2^{High}$ SSEA-$1^{High}$ as compared to $EphA2^{Low}$ SSEA-$1^{low}$ TPCs.

(F) Limiting dilution intracranial transplant of cultured, luciferase-tagged TPCs sorted into $EphA2^{High}$ and $EphA2^{Low}$ pools (top). Light emission imaging analysis (bottom; 5,000, 1,000 and 100 cells per mouse) shows a higher tumor-initiating ability of $EphA2^{High}$ versus $EphA2^{Low}$ TPCs. Error bars, SEM; *p<0.0001, p=0.002, $EphA2^{High}$ vs. $EphA2^{Low}$.

(G) Kaplan-Meier analysis shows that mice receiving $EphA2^{High}$ 1 TPCs die earlier than mice receiving $EphA2^{Low}$ cells (MC and GBW tests, log-rank p-value <0.0001 $EphA2^{High}$ vs. $EphA2^{Low}$; n=9).

FIG. 2: Shows $EphA2^{High}$ TPCs are Enriched in Tumor-initiating Cells and Sustain Tumor Growth in Vivo.

(A-B) Two independent human gliomablastomas tissues were stained, gated and FACS sorted according to EphA2 expression. GBM #23 is shown as an example. Bar, 10 µm.

(C) Intracranial growth of uncultured tumor EphA2 purified populations purified from GBM #23 or GBM #25 tissues and injected at different concentrations in Scid/bg mice. Kaplan-Meier survival curves show that lower dosages ($2 \times 10^4$ or $1 \times 10^4$ cells) of $EphA2^{High}$ purified cells retained the capacity to generate tumors with high efficiency whereas $EphA2^{Low}$ population displayed reduced or null tumorigenic ability. Survival was also shorter when implanting $4 \times 10^4$ $EphA2^{High}$ as compared to $EphA2^{Low}$ cells. (MC and GWB tests, log-rank p-value <0.0001 $EphA2^{High}$ vs. $EphA2^{Low}$ cells; n=8). Tumor growth was assessed over a 6 month period.

(D) Immunohistochemistry for EphA2 (green) and the stem-related CD44 marker (red) in a human glioblastoma (GBM #24). Arrows denote co-localization of proteins (yellow). Inset: no primary antibody. Bar, 10 µm.

(E) Flow plots showing flow cytometric analysis of EphA2 and CD44 in the same glioblastoma sample.

(F) Kaplan-Meier survival analysis showing intracranial growth of EphA2CD44 purified populations derived from GBM #24 tissues and injected at different concentrations in Scid/bg mice. Mice receiving lower dosages ($2 \times 10^4$ or $1 \times 10^4$) of $EphA2^{High}$ $CD44^{High}$ purified TPCs die significantly earlier from tumors (median survival: 162 and 187 days, respectively) than mice receiving $EphA2^{Low}$ $CD44^{Low}$ cells (55% and 73% survival at 190 and 215 days, respectively). MC and GBW tests, log-rank p-value <0.0001 $EphA2^{High}$ $CD44^{High}$ vs. $EphA2^{Low}$ $CD44^{Low}$ cells; n=11. Intracranial transplantation of $4 \times 10^4$ $EphA2^{High}$ $CD44^{High}$ or $EphA2^{Low}$ $CD44^{Low}$ cells confirmed the much higher tumor-propagating capacity of the former. MC and GBW tests, log-rank p-value <0.0001 $EphA2^{High}$ $CD44^{High}$ vs. $EphA2^{Low}$ $CD44^{Low}$ cells; n=11.

(G) Estimated frequency of hGBM TICs in $EphA2^{High}$, $EphA2^{High}$ SSEA-$1^{High}$ and $EphA2^{High}$ $CD44^{High}$ FACS-enriched cell fractions, also as compared to $EphA2^{Low}$, $EphA2^{Low}$ SSEA-$1^{low}$ and $EphA2^{Low}$ $CD44^{Low}$ cells, derived directly from the hGBM patients' specimens and challenged under orthotopic (intracranial) transplantation setting by a limiting dilution assay approach. In all cases, the frequency of hGBM TICs was significantly (p<0.0001) higher in the "high" versus the "low" cell fractions. Median survival is indicated for the lowest dose of cells transplanted.

Figure 3:
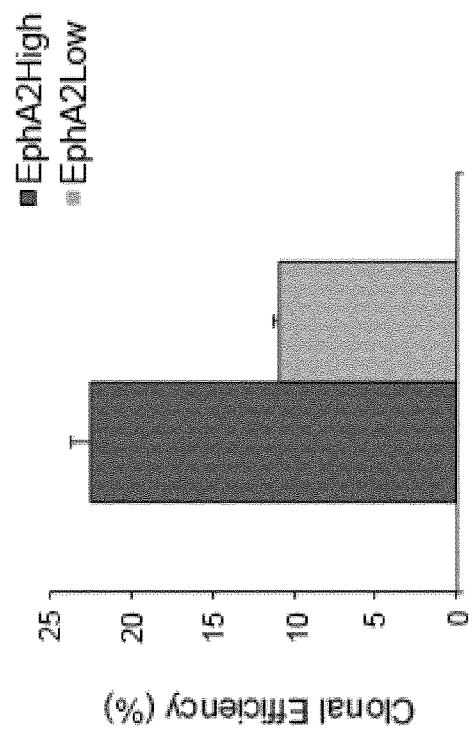
Figure 3:
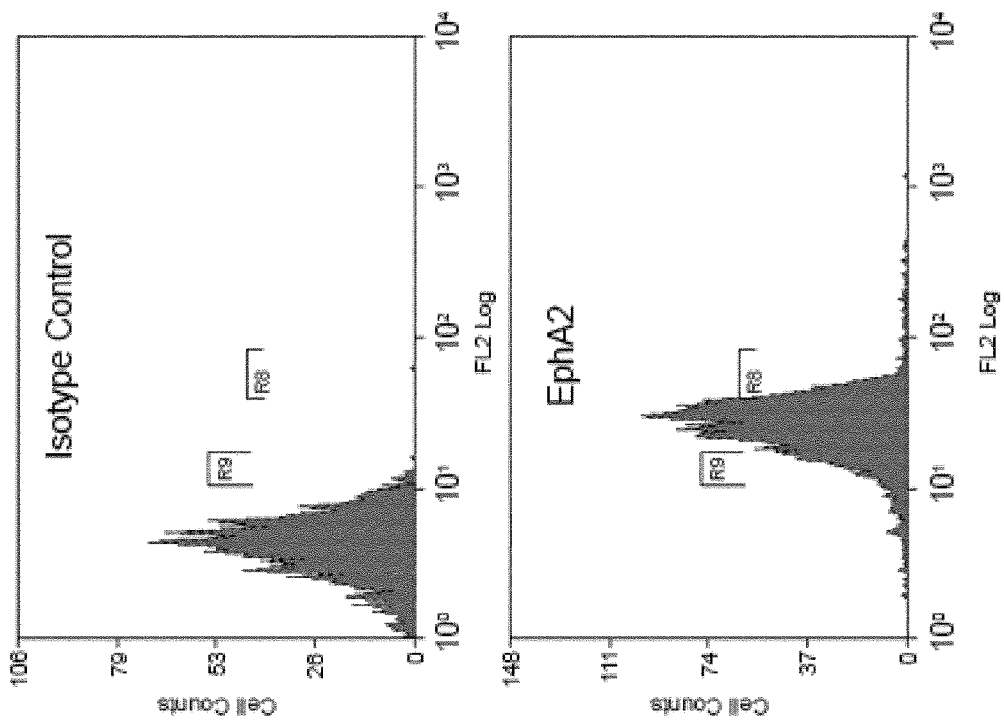

FIG. 3: Shows Enrichment of Established Human Normal Neural Stem Cells Based on EphA2 Levels (A) Human normal neural stem cells were stained, gated and FACS sorted according to EphA2 expression.

(B) Clonal efficiency assay of the human normal neural stem cells, wherein the $EphA2^{High}$ fraction (left column) displayed higher clonogenic index than the $EphA2^{Low}$ fraction (right column).

DETAILED DESCRIPTION OF THE INVENTION

The present invention concerns a method for producing an isolated population of bona fide SCs or TPCs mammalian stem cells comprising the steps of:
a. providing a population of cells,
b. selecting from the population of cells of step a. the cells that express EphA2;
c. isolating the cells selected in step b.,
thereby producing a population of mammalian stem cells.

In the present invention, by an isolated population of cells is intended a group of cells with similar characteristics, such as an undifferentiated and stable phenotype, the capability to expand through multiple passages and to differentiate in multiple cell lineages.

EphA2 (homo sapiens-GeneID: 1969; GI: 32967311; protein_id: NP_004422.2; mus musculus-GeneID: 13836; GI: 32484983; protein_id: NP_034269.2) belongs to the ephrin receptor subfamily of the protein-tyrosine kinase family. Eph and Eph-related receptors have been implicated in mediating developmental events, particularly in the nervous system. The cognate ligand of EphA2 is ephrinA1.

The method according to the present invention has the unexpected advantages of enriching for TPCs by FACS based on high levels of EphA2 expression. Cytofluorimetric sorting into EphA2$^{High}$ and EphA2$^{Low}$ populations demonstrated that EphA2 expression correlates with the size and tumor-propagating ability of the TPC pool in hGBMs.

While studies with glioma cell lines have implicated EphA2 in cell growth and invasiveness, the identity and nature of the actual target cells in the patients' own GBM remain unclear.

In addition, the cellular functions affected by EphA2, the regulatory mechanisms underpinning EphA2's actions in hGBMs pathophysiology and the possibility of manipulating this system to suppress glioma growth are not well characterized. hGBMs contain subpopulations of cells that act as stem-like TPCs, which have now been proven to be crucial therapeutic targets.

Identification and characterization of key regulatory mechanisms in TPCs is crucial for the development of specific therapies for hGBMs. EphA2 abundance in TPCs provides a measure of their stem-like potential and tumor-propagating ability of TPCs from hGBMs. Thus, high EphA2 levels can be used to enrich for TPCs by cell sorting. The method according to the present invention emphasizes the importance of approaches that exploit fundamental similarities in the physiology of normal neural stem cells and their stem-like, tumor-propagating counterpart in brain tumors. Such approaches can make use of the wealth of information derived from studies on regulatory systems in normal neural stem cells to identify candidate effectors capable to affect TPCs, thus helping to design more effective and specific anti-GBM therapies.

In a preferred aspect the invention relates to a method, wherein said population of cells is obtained from a tissue sample, preferably from a biopsy, preferably from a brain biopsy.

In a further aspect the invention relates to a method, wherein said selection step b. is carried out by cell sorting, preferably by Fluorescence-activated cell sorting.

Fluorescence-activated cell sorting (FACS) is a specialized type of flow cytometry. It provides a method for sorting a heterogeneous mixture of biological cells into two or more containers, one cell at a time, based upon the specific light scattering and fluorescent characteristics of each cell.

It is a useful scientific instrument, as it provides fast, objective and quantitative recording of fluorescent signals from individual cells.

Flow sorters have become a widespread and vital resource in the biological sciences and beyond. Their main purpose is to retrieve populations of interest from a heterogeneous population for further study. If a cell or particle can be specifically identified by its physical or chemical characteristics, it can be separated using a flow sorter.

The power of flow cytometry is that it is able to use multiparametric analysis to identify highly specific populations.

In a still further aspect the invention relates to a method, wherein said selection step b. allows to sort the cells according to their EphA2 expression level.

In a further aspect the invention relates to a method, wherein said EphA2 expression level is measured with an anti-EphA2 antibody.

In a still further aspect the invention relates to a method, wherein the mammalian stem cells isolated in step c. are selected from the group consisting of human and mouse bona fide stem cells.

In a still further aspect the invention relates to a method, wherein the human and mouse bona fide stem cells are preferably human or mouse neural stem cells, more preferably human or mouse neural precursors and progenitors.

In a still further aspect the mammalian stem cells isolated in step c of the method of the present invention, are tumor stem cells, preferably brain tumor stem cells, more preferably human glioblastoma multiforme stem cells.

The persistent growth of cancers, clonal diversification and evolution, tumor metastasis and recurrence after therapy may be the consequences of the maintenance by tumor cells of the proliferative potential of stem cells from which the tumor may have originated.

The method of the present invention has the advantages of allowing the isolation of stem cells, which allow to progress toward an understanding of the cellular elements responsible for cancer progression and resistance to treatment. One of the advantages of studying single or defined population of cells, as opposed to large or less defined populations, benefits not only the understanding of the contribution that different populations make towards tumor growth and resistance but also allow a more detailed and accurate mapping of tumor heterogeneity.

Only therapies that efficiently eliminate the stem cell fraction of a tumor are able to induce long-term responses and thereby halt tumor progression.

In a further aspect the invention relates to a method, wherein said EphA2 is a stem cell surface marker.

While cancer stem cells share some properties with normal somatic stem or progenitor cells, they are distinct from the normal stem cells at genetic and molecular signaling levels.

Therefore, the identification of specific markers that are involved in self-renewal and survival of TPCs may be useful to develop novel strategies to improve treatment.

Specifically, blocking distinctive signaling pathways, such as Eph signaling, required in stem cells, should be used to deplete the cancer stem cell population, while traditional chemotherapeutic agents could be used at the same time to de-bulk the larger mass of tumor cells. This will result in a rapid removal of both subpopulations preventing the possibility that some tumor cells could give rise to tumor recurrence. In a further aspect the present invention relates to an isolated population of mammalian bona fide stem cells, obtainable by the method according to the present invention.

The isolation and characterization of multipotent NSCs from multiple locations within the mammalian brain represents one of the most significant advancements in neuroscience and provides accruing evidence of endogenous NSC potential to respond to neurological injuries. This isolated population of mammalian bona fide stem cells has the advantages of overcoming the technical challenge of being easily maintained and cultured in the laboratory and allow for the study of stem cell-based therapies such as those which propose to treat human medical conditions by replacing cells that have been lost or damaged through disease or injury. These cells can be advantageously used to generate stem cell derivatives in the laboratory that have at least some of the properties of normal, mature cell types.

A further aspect of the present invention is the use of the isolated population of mammalian stem cells according to the invention, for the screening of a compound having an inhibiting activity on growth of said stem cells.

Malignant tumors, or at least some of them, comprise cancer stem cells and therefore provide new opportunities at both the experimental and clinical level. In fact, having an isolated population of mammalian stem cells obtained by the method of the present invention allows the investigation of the cells that, although are a minor cell pool within the overall tumor mass, would be the true culprit responsible for establishing, expanding the tumor and perpetuating it following surgery.

A still further aspect of the present invention is the use of EphA2 as a cell surface marker for the identification and the isolation of a stem cell.

Cytofluorimetric sorting into EphA2$^{High}$ and EphA2$^{Low}$ populations demonstrates that EphA2 expression can be used to enrich for both SCs and TPCs and that EphA2 expression correlates with both the size and tumor-propagating ability of the TPC pool in hGBMs.

In a preferred aspect the invention relates to the use of EphA2 as a cell surface marker for the identification and the isolation of a stem cell, wherein said stem cell is a mammalian stem cell, preferably a human or mouse bona fide stem cell.

In a still more preferred aspect, the invention relates to the use of EphA2 as a cell surface marker for the identification and the isolation of a stem cell, wherein stem cell is a tumor stem cell, preferably a brain tumor stem cell, more preferably a glioblastoma multiforme stem cell, still more preferably a human glioblastoma multiforme stem cell.

The effective identification and isolation of a tumor stem cell, in particular of a brain tumor stem cell, where the key pathways that regulate self-renewal and cell fate are believed to be deregulated, leading to uncontrolled self-renewal, would allow to obtain a population of those cancer stem cells which generate and propagate tumors and that are resistant to conventional therapies for a more effective insight into a successful therapy.

EXAMPLES

Example 1

FACS Analysis

Tissues were obtained and classified according to the World Health Organization guidelines. For studies using tumor-derived material, adult human glioblastoma (hGBM) tissues were used, for studies using non-tumor derived material, normal human brain tissues or mouse brain tissues were used. Tissues were dissected and digested in a papain solution and a single-cell suspension was obtained. For cell sorting analysis, cells were centrifuged and resuspended in PBS containing DNase (1 µg/ml; Sigma). Cells were then incubated with the following primary antibodies: goat anti-EphA2 (1:10; R&D Systems) or mouse anti SSEA-1 FITC-conjugated and mouse anti CD44 PE-conjugated (1:15; BD Biosceinces) for 30 min at 4° C., sorted and analyzed (FACSAria, BD Biosciences) using single cell sort mode and Automated Cell Deposition Unit (ACDU). FACSAria was equipped with 488, 633 and violet lasers. Cells were identified and electronically gated on forward and orthogonal light scatter signals (FSC and SSC) and fluorescent signatures (FITC or PE) into separate population based on CD44, SSEA-1 or EphA2 expression. Background fluorescence was estimated by substituting primary antibodies with specific isotype controls. Measurement of autofluorescence was also routinely conducted for each condition tested. The instrument raw data were stored electronically for archiving and data processing.

Culture Cloning

For clonogenic assays, different EphA2-purified single-cell suspension derived from the dissociation of human GBM and normal brain tissue primary stem-like tumor propagating cells or acutely isolated cells) as well as from mouse brain one or from established human normal neural stem cells was plated in single wells by automated FACS and grown as neurospheres. The number of secondary spheres generated was assessed after 7 DIV (Vescovi et al., 1999).

Example 2

Immunohistochemistry

Tissue samples from hGBM, normal human and mouse brain were post-fixed in 4% paraformaldehyde (PFA) for 24 h and placed in a sucrose solution at decreasing concentrations beginning at 30%. Hematoxylin and Eosin (H&E) staining and immunohistochemistry were performed on OCT-embedded, 10 µm-thick cryostat sections (Galli et al., 2004; Vescovi et al., 1999). Tissue sections were stained overnight at 4° C. with the following primary antibodies diluted in 10% normal goat serum (NGS; Gibco, Rockville, Md., USA): mouse anti-EphA2 cloneD7 (1:200; Sigma; St. Louis, Mo., USA), mouse anti-SSEA1 and mouse anti-CD44 (1:100; BD Biosciences, Franklin Lakes, N.J., USA). Goat anti-mouse AlexaFluor488/546 (1:2000; Invitrogen Corp, Carlsbad, Calif., USA) was then employed. Cell nuclei were counterstained by TO-PRO-3 (Molecular Probes, Invitrogen). Negative controls were obtained by omitting primary antibody. Samples were photographed with Zeiss Axioplan2 Microscope and Leica DMIRE2 Confocal Microscope.

Example 3

Evaluation of Tumorigenicity by Orthotopic Implantation

For assays of tumor initiation, primary tumor samples were disaggregated and a single-cell suspension was obtained as described above. 3 µl of a 2×10$^4$ cell/µl of different EphA2-purified cell fractions were injected by stereotaxis into the right striatum of Scid/bg mice as described above (Galli et al., 2004). For the limiting dilution approach, 1×10$^4$, 2×10$^4$ and 4×10$^4$ uncultured tumor-dissociated EphA2, EphA2 SSEA-1 or EphA2 CD44 purified cell fractions or 100, 1,000 and 5,000 different EphA2-purified TPCs populations were injected orthotopically.

Results from in vivo experiments were all subjected to statistical analysis using GraphPad Prism v5.0 software. Survival curves were estimated using the Kaplan-Meier method, with groups compared by respective median survival of number of days taken to reach 50% morbidity. The distributions of survival were compared using the log-rank test. A p-value <0.05 was considered to be statistically significant.

The estimated frequency of tumor-initiating cells was determined according to published methods (Hu and Smyth, 2009).

Example 4

TPCs Lentiviral Infection

Cells were infected with reporter gene firefly luciferase (Amendola et al., 2005). Vector's expression titer was estimated on Hela cells by limiting dilution. Vector particles were measured by HIV-1 gag p24 antigen immunocapture. Vector infectivity was calculated as the ratio between titer and particle for each vector. TPCs were exposed for 16 h to the supernatant, conditioned by transfected 293T cells overnight. Medium containing virus was then removed and replaced by fresh medium. The efficiency of infection was assessed by In vivo Lumina analysis. Bioluminescent cells were serially diluted from 5000 to 100 cells in culture medium into black, clear bottomed, 96-well plates. D-luciferin (ONE-Glo, luciferase assay system, Promega) was added 1:1 (vv) to each well 3 min before imaging. Imaging time was 1min\plate.

Example 5

Analysis of Tumor Progression in Vivo

TPCs tumorigenicity, tumor formation, extension and volume were indirectly calculated by sequential images taken with In Vivo Lumina analysis (Xenogen, Caliper Life Sciences, Hopkinton, Mass., USA). Animals were given the substrate D-luciferin (Caliper Life Sciences) by intraperitoneal injection at 150 mg/Kg 15 min before imaging and then anesthetized (2.5% isofluorane) (Jenkins et al., 2005). Mice were placed onto the warmed stage inside the light-tight camera box with continuous exposure to 2% isofluorane. Luminescent measures were performed once a week. The low levels of light emitted from bioluminescent tumors were detected by the IVIS TM camera system, integrated, digitized, and displayed. Pseudocolor scale bars were consistent for all images of dorsal views in order to show relative changes at tumor site over time. Region of interest (ROI) from displayed images were identified around the tumor sites and were quantified as total flux (photons/s/cm$^2$) using Living Image software (Xenogen, Caliper Life Sciences).

From the above description and the above-noted examples, the advantage attained by the method described and obtained according to the present invention are apparent.

REFERENCES

Vescovi, A. L., Parati, E. A., Gritti, A., Poulin, P., Ferrario, M., Wanke, E., Frolichsthal-Schoeller, P., Cava, L., Arcellana-Panlilio, M., Colombo, A., and Galli, R. (1999). Isolation and cloning of multipotential stem cells from the embryonic human CNS and establishment of transplantable human neural stem cell lines by epigenetic stimulation. Experimental neurology 156, 71-83.

Galli, R., Binda, E., Orfanelli, U., Cipelletti, B., Gritti, A., De Vitis, S., Fiocco, R., Foroni, C., DiMeco, F., and Vescovi, A. (2004). Isolation and characterization of tumorigenic, stem-like neural precursors from human glioblastoma. Cancer Res 64, 7011-7021.

Hu, Y., and Smyth, G. K. (2009). ELDA: extreme limiting dilution analysis for comparing depleted and enriched populations in stem cell and other assays. J. Immunol. Methods 347, 70-78.

Amendola, M., Venneri, M. A., Biffi, A., Vigna, E., and Naldini, L. (2005). Coordinate dual-gene transgenesis by lentiviral vectors carrying synthetic bidirectional promoters. Nat Biotechnol 23, 108-116.

Jenkins, D. E., Hornig, Y. S., Oei, Y., Dusich, J., and Purchio, T. (2005). Bioluminescent human breast cancer cell lines that permit rapid and sensitive in vivo detection of mammary tumors and multiple metastases in immune deficient mice. Breast Cancer Res 7, R444-454.

The invention claimed is:

1. A method for isolating and enriching a subpopulation of tumor-propagating cells (TPCs) or cancer stem cells (CSCs) from a brain tumor comprising:
    (a) obtaining a tissue sample from a brain tumor comprising a population of tumor cells comprising a subpopulation of TPCs or CSCs;
    (b) dissociating the tissue sample to obtain a single-cell suspension;
    (c) staining the tumor cells for expression of EphA2 and one or more of CD44 and SSEA-1; and
    (d) separating the subpopulation of TPCs or CSCs characterized by a high level of expression of EphA2 (EphA2$^{High}$) from the subpopulation of TPCs or CSCs characterized by a low level of expression of EphA2 (EphA2$^{Low}$), wherein the high level of expression of EphA2 (EphA2$^{High}$) is the highest 10% of expression relative to mean EphA2 expression of the subpopulation and the low level of expression of EphA2 (EphA2$^{Low}$) is the lowest 10% of expression relative to mean EphA2 expression of the subpopulation.

2. The method according to claim 1, wherein the brain tumor is a malignant brain tumor.

3. The method according to claim 2, wherein the malignant brain tumor is a glioma.

4. The method according to claim 3, wherein the glioma is a glioblastoma multiforme.

5. The method according to claim 1, wherein separating step (d) is performed by cell sorting.

6. The method according to claim 5, wherein separating step (d) is performed by flow cytometry.

7. The method according to claim 6, wherein the flow cytometry is fluorescence-activated cell sorting (FACS).

8. The method according to claim 1, wherein step (c) further comprises tagging the tumor cells with fluorescently labeled antibodies which bind specifically to EphA2.

9. The method according to claim 8, wherein the staining of step (c) is fluorescence staining and step (d) further comprises selecting TPCs or CSCs which have mean fluorescence values for EphA2 surface antigen of at least two logs greater than that of isotype controls.

10. The method according to claim 1, wherein the tissue sample from a brain tumor is a brain tumor biopsy.

11. The method according to claim 10, wherein the brain tumor biopsy is a biopsy from a glioblastoma.

12. The method according to claim 1, wherein the TPCs or CSCs are human TPCs or CSCs.

13. The method according to claim 1, wherein the TPCs or CSCs are mouse TPCs or CSCs.

14. The method according to claim 1, wherein the EphA2$^{High}$ TPCs or CSCs have a clonogenic index higher than a clonogenic index of EphA2$^{Low}$ TPCs or CSCs.

15. The method according to claim 1, further comprising culturing the TPCs or CSCs characterized by EphA2$^{High}$ in vitro.

* * * * *